US012133985B2

(12) United States Patent
Bornhoft et al.

(10) Patent No.: US 12,133,985 B2
(45) Date of Patent: *Nov. 5, 2024

(54) FAR FIELD TELEMETRY COMMUNICATION WITH A MEDICAL DEVICE DURING A RECHARGE SESSION WHERE A PRIOR PAIRING WITH THE MEDICAL DEVICE MAY NOT EXIST

(71) Applicant: MEDTRONIC, INC., Minneapolis, MN (US)

(72) Inventors: Reid K. Bornhoft, Lino Lakes, MN (US); Garrett R. Sipple, Circle Pines, MN (US); Nathan A. Torgerson, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 530 days.

This patent is subject to a terminal disclaimer.

(21) Appl. No.: 17/132,681

(22) Filed: Dec. 23, 2020

(65) Prior Publication Data

US 2021/0138253 A1 May 13, 2021

Related U.S. Application Data

(60) Continuation of application No. 16/146,929, filed on Sep. 28, 2018, now Pat. No. 10,881,865, which is a
(Continued)

(51) Int. Cl.
*A61N 1/08* (2006.01)
*A61N 1/372* (2006.01)
*A61N 1/378* (2006.01)

(52) U.S. Cl.
CPC ....... *A61N 1/37252* (2013.01); *A61N 1/3787* (2013.01)

(58) Field of Classification Search
CPC .............. A61N 1/3787; A61N 1/37229; A61N 1/37217; A61N 1/37223
See application file for complete search history.

(56) References Cited

U.S. PATENT DOCUMENTS

| 5,107,833 A | 4/1992 | Barsness |
| 5,733,313 A | 3/1998 | Barreras et al. |
| (Continued) | | |

FOREIGN PATENT DOCUMENTS

| EP | 2092958 | 8/2009 |
| WO | 2003039652 | 1/2004 |
| (Continued) | | |

OTHER PUBLICATIONS

Partial International Search Report issued in PCT/US2011/054002 on Dec. 23, 2011.
(Continued)

*Primary Examiner* — Michael J D'Abreu
(74) *Attorney, Agent, or Firm* — Shumaker & Sieffert, P.A.

(57) ABSTRACT

Far field telemetry communications are conducted during recharge sessions between an external device and an implantable medical device. The two devices may not have been previously paired together for far field telemetry and may have been paired with other devices for far field telemetry during previous recharge sessions and/or programming sessions. Embodiments provide for temporary bonding of the two devices for far field telemetry during the recharge session. The implantable medical device of the recharge session may maintain a programming bond with an external device other than the external device conducting the recharge session. Safeguards against establishment of inadvertent programming sessions between the external device that has conducted a recharge session and implantable
(Continued)

medical devices that may or may not be bonded to that external device are provided.

20 Claims, 11 Drawing Sheets

Related U.S. Application Data division of application No. 13/016,793, filed on Jan. 28, 2011, now Pat. No. 10,286,217.

(56) References Cited

U.S. PATENT DOCUMENTS

| | | | |
|---|---|---|---|
| 5,735,887 A | 4/1998 | Barreras et al. | |
| 5,755,748 A | 5/1998 | Borza | |
| 6,212,430 B1 | 4/2001 | Kung | |
| 6,263,247 B1 | 7/2001 | Mueller et al. | |
| 6,308,099 B1* | 10/2001 | Fox | A61N 1/37252 607/30 |
| 6,345,203 B1 | 2/2002 | Mueller et al. | |
| 6,430,444 B1 | 8/2002 | Borza | |
| 6,631,296 B1 | 10/2003 | Parramon et al. | |
| 7,138,902 B2 | 11/2006 | Menard | |
| 7,406,105 B2 | 7/2008 | Delmain et al. | |
| 7,471,986 B2 | 12/2008 | Hatlestad | |
| 7,664,553 B2 | 2/2010 | Roberts | |
| 8,634,927 B2 | 1/2014 | Olson et al. | |
| 8,712,541 B2 | 4/2014 | Olson | |
| 9,318,916 B2 | 4/2016 | Olson | |
| 9,393,434 B2 | 7/2016 | Olson | |
| 9,729,001 B2 | 8/2017 | Olson | |
| 2003/0078634 A1 | 4/2003 | Schulman et al. | |
| 2003/0114898 A1 | 6/2003 | Von Arx | |
| 2005/0204134 A1* | 9/2005 | Von Arx | H04L 9/0891 713/168 |
| 2007/0060980 A1* | 3/2007 | Strother | A61N 1/3787 607/34 |
| 2007/0129767 A1 | 6/2007 | Wahlstrand | |
| 2007/0150019 A1 | 6/2007 | Youker | |
| 2008/0058900 A1 | 3/2008 | Berthelsdorf et al. | |
| 2008/0109051 A1 | 5/2008 | Splinter et al. | |
| 2008/0300660 A1 | 12/2008 | Sasha | |
| 2009/0073991 A1 | 3/2009 | Landrum et al. | |
| 2009/0118796 A1 | 5/2009 | Chen et al. | |
| 2009/0182388 A1 | 7/2009 | Von Arx et al. | |
| 2009/0259723 A1 | 10/2009 | Figueiredo et al. | |
| 2009/0270948 A1 | 10/2009 | Nghien | |
| 2010/0106223 A1 | 4/2010 | Grevious et al. | |
| 2010/0114216 A1 | 5/2010 | Krause et al. | |
| 2010/0305663 A1 | 12/2010 | Aghassian | |
| 2012/0150259 A1 | 6/2012 | Meskens | |
| 2012/0197347 A1 | 8/2012 | Olson | |
| 2012/0197351 A1 | 8/2012 | Olson | |
| 2014/0163648 A1 | 6/2014 | Olson | |
| 2014/0221767 A1 | 8/2014 | Olson | |
| 2016/0164337 A1 | 6/2016 | Olson | |
| 2017/0317518 A1 | 11/2017 | Olson | |

FOREIGN PATENT DOCUMENTS

| | | |
|---|---|---|
| WO | 2008069829 | 6/2008 |
| WO | 2009055203 | 4/2009 |
| WO | 2009055579 | 4/2009 |
| WO | 2010051485 | 5/2010 |
| WO | 2011034681 | 3/2011 |
| WO | 2011059643 | 5/2011 |
| WO | 2011079309 | 6/2011 |

OTHER PUBLICATIONS

International Search Report and Written Opinion, issued in PCT/US2011/054002 on Apr. 19, 2012.
International Search Report and Written Opinion issued in PCT/US2011/051921 on Feb. 19, 2013.
Budgett, David M. et al., Novel Technology for the Provision of Power to Implantable Physiological Devices, Journal of Applied Physiology, vol. 102, No. 4, pp. 1658-1663, Apr. 1, 2007.
U.S. Appl. No. 13/016,711, filed Jan. 28, 2011.
U.S. Appl. No. 13/016,711, Restriction Requirement dated Dec. 13, 2012.
U.S. Appl. No. 13/016,711, Response to Restriction Requirement filed Jan. 4, 2013.
U.S. Appl. No. 13/016,711, Office Action dated Jan. 23, 2013.
U.S. Appl. No. 13/016,711, Response to Office Action filed Apr. 23, 2013.
U.S. Appl. No. 13/016,711, Final Office Action dated Jul. 16, 2013.
U.S. Appl. No. 13/016,711, Response to Office Action filed Sep. 10, 2013.
U.S. Appl. No. 13/016,711, Notice of Allowance Sep. 17, 2013.
U.S. Appl. No. 14/135,201, filed Dec. 19, 2013.
U.S. Appl. No. 14/135,201, Restriction Requirement dated Mar. 24, 2014.
U.S. Appl. No. 14/135,201 Response filed Apr. 24, 2014.
U.S. Appl. No. 14/135,201, Office Action dated May 5, 2014.
U.S. Appl. No. 14/135,201 Response filed Aug. 5, 2014.
U.S. Appl. No. 14/135,201 Final Office Action dated Oct. 1, 2014.
U.S. Appl. No. 14/135,201 Response filed Dec. 1, 2014.
U.S. Appl. No. 14/135,201 Advisory Action dated Dec. 9, 2014.
U.S. Appl. No. 14/135,201 RCE Response filed Dec. 29, 2014.
U.S. Appl. No. 14/135,201 Office Action dated Jul. 15, 2015.
U.S. Appl. No. 14/135,201 Response Filed Oct. 15, 2015.
U.S. Appl. No. 14/135,201 Final Office Action dated Jan. 4, 2016.
U.S. Appl. No. 14/135,201 Response filed Mar. 4, 2016.
U.S. Appl. No. 14/135,201 Notice of Allowance dated Mar. 16, 2016.
U.S. Appl. No. 13/016,763 Restriction Requirement dated Jun. 17, 2013.
U.S. Appl. No. 13/016,763 Response filed Jul. 29, 2013.
U.S. Appl. No. 13/016,763 Office Action dated Aug. 20, 2013.
U.S. Appl. No. 13/016,763 Response filed Nov. 19, 2013.
U.S. Appl. No. 13/016,763 Notice of Allowance dated Dec. 11, 2013.
U.S. Appl. No. 14/246,071, filed Apr. 5, 2014.
U.S. Appl. No. 14/246,071 Office Action dated Nov. 13, 2014.
U.S. Appl. No. 14/246,071 Response filed Feb. 13, 2015.
U.S. Appl. No. 14/246,071 Final Office Action dated Mar. 19, 2015.
U.S. Appl. No. 14/246,071 Response filed May 19, 2015.
U.S. Appl. No. 14/246,071 Advisory Action dated Jun. 1, 2015.
U.S. Appl. No. 14/246,071 Notice of Appeal Filed Jun. 19, 2012.
U.S. Appl. No. 14/246,071 Notice of Allowance dated Aug. 17, 2015.
U.S. Appl. No. 14/246,071 RCE Request filed Nov. 15, 2015.
U.S. Appl. No. 14/246,071 Notice of Allowance dated Dec. 10, 2015.
U.S. Appl. No. 15/042,073, filed Feb. 11, 2016.
U.S. Appl. No. 15/042,073 Office Action dated Oct. 6, 2016.
U.S. Appl. No. 15/042,073 Response filed Jan. 6, 2017.
U.S. Appl. No. 15/042,073 Notice of Allowance Mar. 29, 2017.
U.S. Appl. No. 15/650,598, filed Jul. 14, 2017.
U.S. Appl. No. 15/650,598 Office Action dated Apr. 4, 2018.
U.S. Appl. No. 15/650,598 Response file Jul. 5, 2016.
U.S. Appl. No. 15/650,598 Notice of Allowance dated Aug. 27, 2018.
U.S. Appl. No. 16/215,918, filed Dec. 11, 2018.
U.S. Appl. No. 16/215,918 Office Action dated Apr. 30, 2020.
U.S. Appl. No. 16/215,918 Response and Terminal Disclaimer Filed Jul. 27, 2020.
U.S. Appl. No. 16/215,918 Notice of Allowance dated Sep. 21, 2020.
U.S. Appl. No. 17/129,758, filed Dec. 21, 2020.
U.S. Appl. No. 16/146,929, filed Sep. 28, 2018.
U.S. Appl. No. 16/146,929 Office Action dated Sep. 19, 2019.
U.S. Appl. No. 16/146,929 Response filed Dec. 12, 2019.
U.S. Appl. No. 16/146,929 Final Office Action dated Apr. 3, 2020.
U.S. Appl. No. 16/146,929 Response-RCE Filed Jun. 30, 2020.

(56) References Cited

OTHER PUBLICATIONS

U.S. Appl. No. 16/146,929 Notice of Allowance dated Sep. 8, 2020.

* cited by examiner

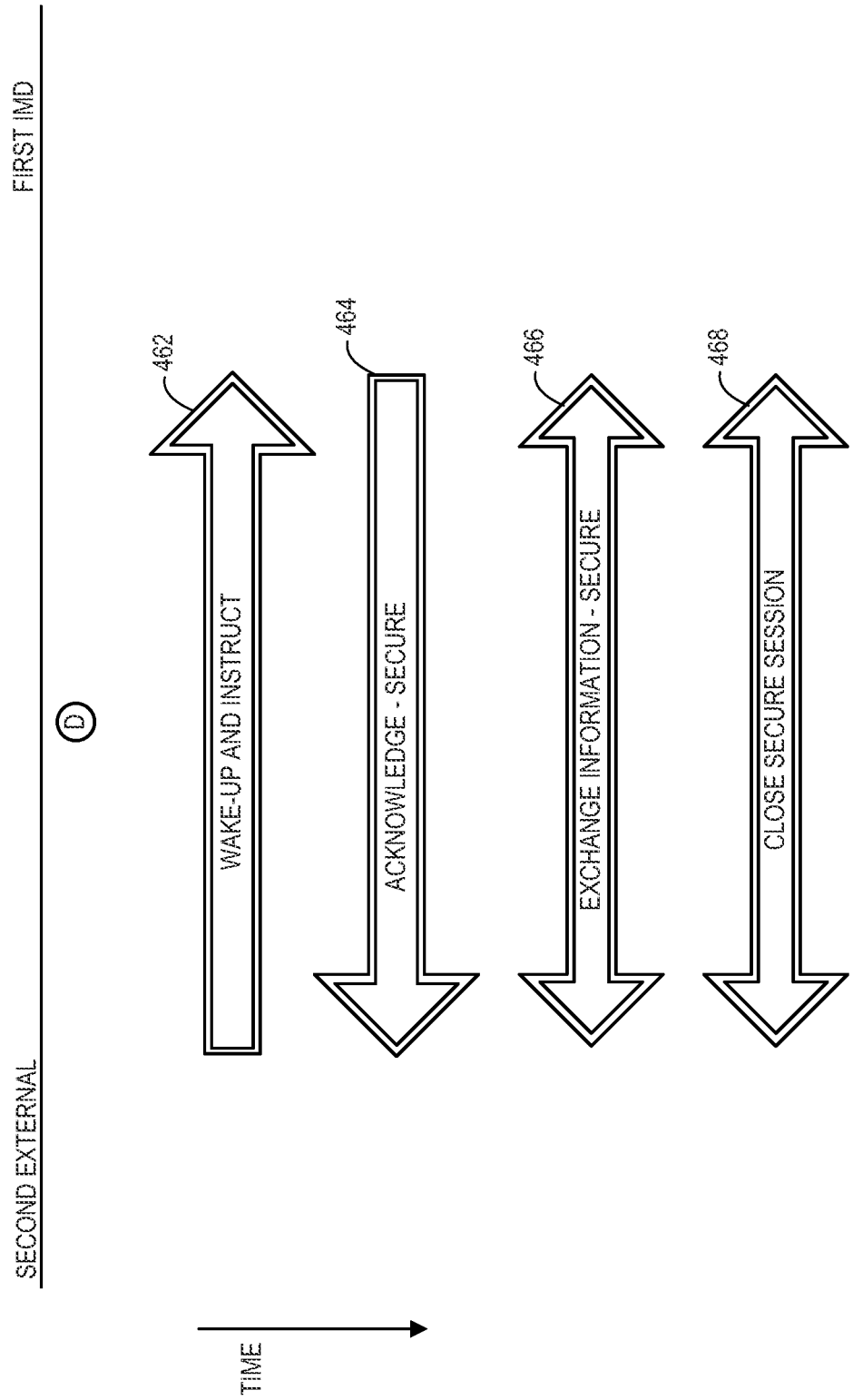

FAR FIELD TELEMETRY COMMUNICATION WITH A MEDICAL DEVICE DURING A RECHARGE SESSION WHERE A PRIOR PAIRING WITH THE MEDICAL DEVICE MAY NOT EXIST

TECHNICAL FIELD

Embodiments relate to recharge sessions between an implantable medical device to be recharged and an external device in control of the recharge energy. More particularly, embodiments relate to conducting far field telemetry communications between the implantable medical device and the external device during a recharge session where the implantable medical device and the external device may not have been previously paired for the far field telemetry communications.

BACKGROUND

Implantable medical devices including those that are positioned on the exterior of a body of a patient as well as those that are positioned subcutaneously or deeper typically utilize an on-board battery that allows the patient to be untethered to a power source. The patient maintains mobility while the implantable medical device performs a particular medical task by operating on power from the battery. For instance, the implantable medical device may provide stimulation therapy for neurological or cardiac conditions, may provide drug delivery for various conditions such as pain management, and/or may provide physiological monitoring.

While the on-board battery may power the medical device for a relatively long period of time, the on-board battery will eventually be depleted. Prior to rechargeable medical systems, the implantable medical device would be replaced once the battery became depleted. With rechargeable medical systems, an external device provides recharge energy over a proximity coupling, which is typically inductive, to the implantable medical device. This recharge energy restores the on-board battery to a satisfactory level for continued operation of the medical device.

During a recharge session, the external device in control of the recharge energy and the implantable medical device to be recharged exchange telemetry communications related to the recharge process. Recharge information such as battery status, coupling efficiency and the like may be transferred in this manner so that the external device can properly control delivery of the recharge energy as well as instruct a user. Conventionally, the two devices exchange telemetry communications over a proximity coupling. However, far field telemetry communications using radio frequency communications such as those in the Medical Implant Communication Service (MICS) band allow for far field telemetry communications between the external device and the implantable medical device.

While far field telemetry communications may be employed during a recharge session for one or more reasons, such as to provide convenience to the users and/or to increase the efficiency of the recharge process by using a proximity coupling only for recharge energy delivery, issues may also arise. Because far field telemetry communications are capable of extending to other external devices and implantable devices in the vicinity, far field telemetry communications typically call for a pairing to exist between devices in the form of a bond, where that bond may be implemented as knowledge of an identifier of the other device and/or a shared encryption key. For systems where a prior bond is necessary to establish a recharge session, if one of the two devices involved in an attempted recharge session is already paired with another device, then the recharge attempt may present additional issues, such as a failure of the recharge session to commence, failure to communication recharge information over far field telemetry communications, and so forth. Examples of situations where this may arise include the case of one user's patient therapy module attempting to recharge another user's implantable medical device, an external device of a sales representative or clinician attempting to recharge a patient's implant, and so forth.

SUMMARY

Embodiments address issues such as these and others by providing the establishment of far field telemetry communications between an implantable medical device to be recharged and an external device in control of the recharge energy during a recharge session when a prior pairing of the two devices may not exist. A temporary pairing may be created for the duration of the recharge session and be unavailable for subsequent recharge sessions where a new temporary pairing would occur. This pairing may be in addition to any additional pairings one or both devices involved in the recharge session may possess, such as where either the external device, the implantable medical device, or both devices possess programming bonds with other devices that survive longer than any one programming session. The external device may delete a programming bond with other devices during a recharge session with a guest device so that once a recharge session has completed there is no inadvertent programming session with the originally paired device while a user of the guest device has control of the external device. Furthermore, the external device may provide a notice to a user when an implantable medical device is being recharged that lacks a prior pairing with the external device.

Embodiments provide a method of creating a recharging session between an implantable medical device to be recharged and an external device. The method involves storing at the external device a programming session key and an identifier of a program bonded implantable medical device and exchanging an identifier of the implantable medical device to be recharged between the external device and the implantable medical device to be recharged. The method further involves beginning a recharge session through a proximity wireless recharge coupling between the external device and the implantable medical device to be recharged and exchanging information related to the recharge session over a far field telemetry connection between the external device and the implantable medical device to be recharged. The method further involves detecting whether the identifier of the implantable medical device to be recharged matches the identifier of the program bonded implantable medical device, and if the identifier of the implantable medical device to be recharged does not match the identifier of the program bonded implantable medical device, then deleting the programming session key stored at the external device.

Embodiments provide a method of creating a recharging session between an implantable medical device to be recharged and an external device that involves exchanging a recharge key between the external device and the implantable medical device to be recharged and beginning a recharge session through a proximity wireless recharge coupling between the external device and the implantable medical device to be recharged. The method further involves exchanging information related to the recharge session over a far field telemetry connection between the external device and the implantable medical device to be recharged using the recharge key, and discontinuing current and future use of the recharge key upon termination of the recharge session.

Embodiments provide a method of creating a recharging session between an implantable medical device to be recharged and an external device. The method involves storing at the external device an identifier of a program bonded implantable medical device and exchanging an identifier of the implantable medical device to be recharged between the external device and the implantable medical device to be recharged. The method further involves providing an external annunciation indicating whether the implantable medical device to be recharged is the program bonded implantable medical device based on a comparison of the stored identifier to the exchanged identifier. The method additionally involves beginning a recharge session through a proximity wireless recharge coupling between the external device and the implantable medical device to be recharged and exchanging information related to the recharge session over a far field telemetry connection between the external device and the implantable medical device to be recharged.

Embodiments provide an implantable medical device that includes a memory storing an identifier and a programming session key, a recharge circuit, a battery coupled to the recharge circuit, a far field telemetry circuit, and a processor. The processor is configured to receive a recharge session key from an external device, provide an identifier to the external device, and receive recharge energy during a recharge session using the recharge circuit. The processor is also configured to exchange information related to the recharge session with the external device using the recharge key via the far field telemetry circuit while the programming session key remains stored in the memory, and at times other than during the recharge session exchange programming information with a second external device using the programming session key via the far field telemetry circuit.

Embodiments provide a medical system that includes an implantable medical device to be recharged and an external device. The external device stores a programming session key and an identifier of a program bonded implantable medical device and receives an identifier of the implantable medical device to be recharged from the implantable medical device to be recharged. The external device also begins a recharge session through a proximity wireless recharge coupling between the external device and the implantable medical device to be recharged and exchanges information related to the recharge session over a far field telemetry connection between the external device and the implantable medical device to be recharged. Additionally, the external device detects whether the identifier of the implantable medical device to be recharged matches the identifier of the program bonded implantable medical device and if the identifier of the implantable medical device to be recharged does not match the identifier of the program bonded implantable medical device, then deletes the programming session key stored at the external device.

Embodiments provide a medical system that includes an implantable medical device to be recharged and an external device. The external device exchanges a recharge key with the implantable medical device to be recharged and begins a recharge session through a proximity wireless recharge coupling between the external device and the implantable medical device to be recharged. The external device also exchanges information related to the recharge session over a far field telemetry connection between the external device and the implantable medical device to be recharged using the recharge key, and discontinues current and future use of the recharge key upon termination of the recharge session.

Embodiments provide a medical system that includes an implantable medical device to be recharged and an external device. The external device stores an identifier of a program bonded implantable medical device and receives an identifier of the implantable medical device to be recharged from the implantable medical device to be recharged. The external device provides an external annunciation indicating whether the implantable medical device to be recharged is the program bonded implantable medical device based on a comparison of the stored identifier to the exchanged identifier. The external device also begins a recharge session through a proximity wireless recharge coupling between the external device and the implantable medical device to be recharged and exchanges information related to the recharge session over a far field telemetry connection between the external device and the implantable medical device to be recharged.

DESCRIPTION OF THE DRAWINGS

FIGS. 4A-4F show an example of operations of the external device and implantable medical device of the medical system.

DETAILED DESCRIPTION

Embodiments provide for far field telemetry communications during recharge sessions between an external device and an implantable medical device. The two devices may not have been previously paired together and may have been paired with other devices for previous recharge sessions and/or programming sessions. Embodiments provide for temporary bonding of the two devices for the recharge session. Embodiments further provide for the implantable medical device of the recharge session to maintain a distant telemetry bond with an external device other than the external device conducting the recharge session. Embodiments further provide safeguards against establishment of inadvertent programming sessions between the external device that has conducted a recharge session and implantable medical devices that may or may not be bonded to that external device.

Figure 1:
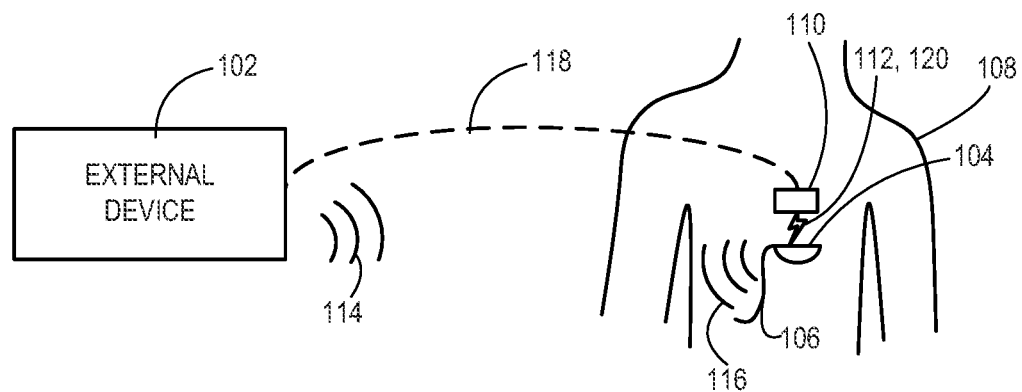
FIG. 1 shows an example of a medical system according to various embodiments.

FIG. 1 shows an environment that includes an external device 102, such as a clinician programmer-recharger or a patient programmer-recharger that is nearby a patient 108 who has an IMD 104. The IMD 104 may be implanted within or mounted externally to the body 108 and may perform one or more medical tasks such as cardiac or neurological stimulation, physiological sensing, drug infusion, and the like. The IMD 104 may include components 106 such as stimulation or sensing leads or drug delivery catheters that extend from the IMD 104 and terminate at the target area of the body 108.

The patient 108 ultimately wants the IMD 104 to be recharged so that medical therapy can continue. The external device 102 may provide various functions including a recharge function whereby a recharge session is established between the external device 102 and the IMD 104. During the recharge session, recharge energy is provided while a communication session is also conducted to allow the external device 102 to receive feedback about charging status from the IMD 104.

The external device 102 ultimately communicates with the IMD 104 during a recharge session through a far field telemetry communication session utilizing far field signals 114 sent by the external device 102 and far field signals 116 sent by the IMD 104. These far field signals 114, 116 may be radio frequency (RF) signals such as those of the Medical Implant Communications Service (MICS) band, the Industrial, Scientific, and Medical (ISM) band, or the short range device (SRD) band. The far field telemetry communication session may be used for additional purposes during the recharge session as discussed below. Far field telemetry communications are those where a wave, i.e., via an E-field, is propagated and that wave may be used to carry the communications as opposed to relying on an inductive coupling, i.e., via an H-field.

While the single IMD 104 is shown in FIG. 1, it will be appreciated that there may be other IMDs and/or other external devices nearby and in range of the far field signals 114 of the external device 102. While the external device 102 may already share a programming bond with a particular IMD, the IMD 104 to be recharged may not be the IMD that has the programming bond. For instance, one patient who owns the external device 102 may loan it to another patient 108 to allow the external device 102 to recharge the IMD 104 even though the IMD 104 is not program bonded to the external device 102. As another example, a sales representative or other clinician may have an external device 102 that may conduct a recharge session with IMDs from many different patients during office visits, where the external device 102 does not have a program bond with any IMD.

The external device 102 may or may not be aware of identification information of the intended IMD 104 in advance such that the external device 102 cannot immediately discern far field telemetry communications of the intended IMD 104 relative to far field telemetry communications of other IMDs. However, physical proximity can be established to allow proximity communication 112 and/or recharge energy transfer 120 to occur between the external device 102 and the intended IMD 104. Physical proximity refers to the intended IMD 104 being positioned closely to the external device 102 to the extent that an observer such as a clinician can confirm that the intended IMD 104 is the only IMD that can be responsive to proximity communications. Where the proximity communication is a signal from proximity telemetry, the proximity telemetry communications are those where the signal is typically an inductively coupled signal transfer, i.e., via an H-field. For proximity telemetry, the external device 102 must be within physical proximity of the IMD (i.e., within the patient's "personal space") for the IMD to communicate with the external device. This is opposed to far field communications wherein external device 102 may, but need not, be within physical proximity of the IMD to communicate with the IMD.

Therefore, a procedure is provided that utilizes this physical proximity at the initiation of the far field telemetry communication session and related recharge session to avoid the external device 102 conducting a far field telemetry communication session with an unintended nearby IMD while recharging the intended IMD 104. To allow the external device 102 to select the intended IMD 104 for far field telemetry communication during a recharge session and avoid selecting an unintended nearby IMD, proximity communication signals 112 may be exchanged between a proximity communicator 110 and the IMD 104 during the establishment of the far field telemetry communication session.

The proximity communicator 110 may be of various forms and may be a separate component of the external device 102 or be integrated with the external device 102, or a combination of both. For instance, the proximity communicator 110 may be a near field telemetry head that is tethered to the external device 102 by a communication path 118 such as a cable or wireless connection and that establishes an inductive link with the IMD 104. The proximity communicator 110 may utilize the transfer of recharge energy as a proximity communication. As another example, the proximity communicator 110 may be an audible tone generator where the IMD 104 receives and recognizes different audible tones. As another example, the proximity communicator 110 may be a body thump device, such as a chest thump device, where the IMD 104 detects the thump through an on-board accelerometer or other vibration detector. As yet another example, the proximity communicator 110 may be a static field generating device such as an electromagnet or a permanent magnet being moved into and out of proximity with the IMD 104 by the clinician.

In some cases including the near field telemetry head, the audible signal generator, the body thump device, and the electromagnet, the proximity communicator 110 may be under control of the external device 102 through a tethered or wireless connection between the telemetry head 110 and the external device 102. In some cases including the clinician providing the body thump or moving the permanent magnet, the proximity communicator 110 is under direct control of the clinician who may be following commands being issued by the external device 102 to provide or remove the proximity communication.

The proximity communicator 110 may also integrate recharge circuitry including a recharge coil that inductively couples to a coil of the IMD 104 to inductively transfer energy. Thus, a single tool may be placed in physical proximity of the patient 108 in order to establish a form of proximity communication and to delivery recharge energy. Where the connection 118 is wired, recharge energy may be sourced from the external device 102. Where the connection 118 is wireless, the recharge energy may be sourced from an on-board power supply of the proximity communicator 110. As an alternative, the recharge device may be a separate device from the proximity communicator 110 where both are held in physical proximity to the patient 108 and linked to the external device 102.

The proximity communication may range from being a simple present or absent signal to a more complex signal carrying data. Furthermore, the proximity communication may be a unidirectional communication mode in some embodiments, particularly where the communication is simple. This may reduce the cost and complexity of a device, particularly the IMD 104. One particular example of proximity communication may be the presence or absence of recharge energy, and this recharge energy may be pulsed in accordance with a particular pattern that the IMD 104 may discern and which the IMD 104 may echo back to the external device 102. The proximity communication may be a bi-directional communication mode in other embodiments, such as where one device may send data through a proximity communication while the other device may send an acknowledgement through a subsequent proximity communication. This may improve the efficiency of the proximity communication procedure.

Figure 2:
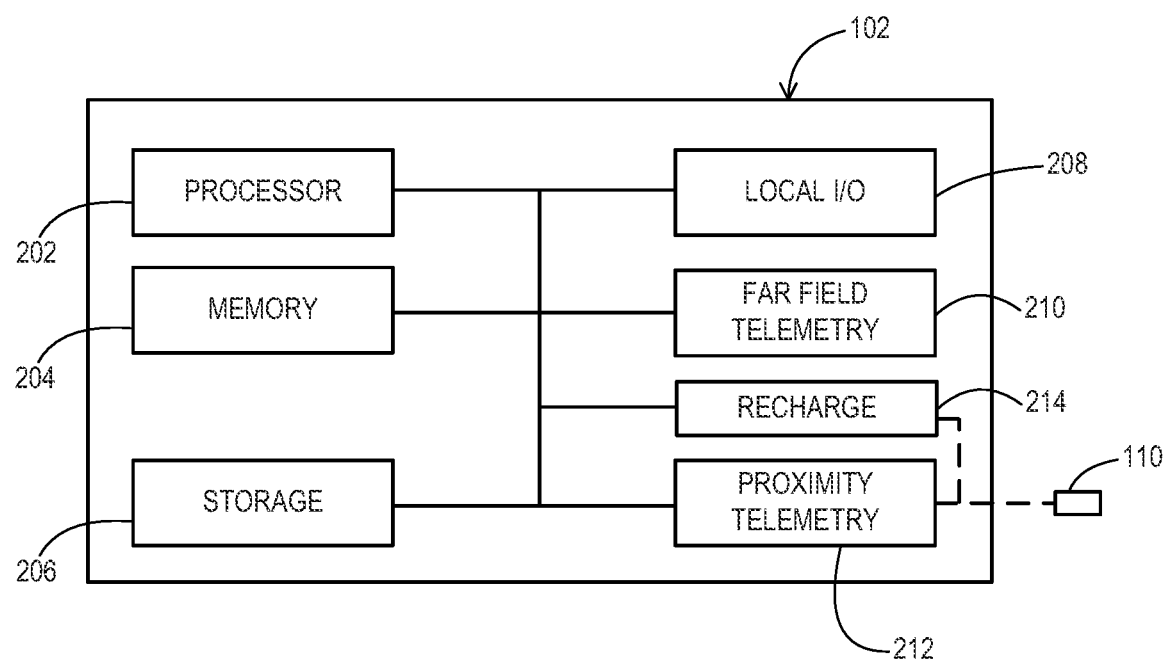
FIG. 2 shows an example of components of an external device of the medical system.

FIG. 2 shows components of one example of the external device 102. The external device 102 includes a processor 202, a memory 204, and a storage device 206. The external device 102 may also include local input/output (I/O) ports 208 such as to provide local screen displays and to receive user input via keyboard, mouse, and so forth. The external device 102 also includes far field telemetry communication circuitry 210 used to establish the far field telemetry communication session with the IMD 104. The far field telemetry communication circuitry 210 may drive a signal propagation tool such as an RF antenna. The signal propagation tool may be included within the proximity communicator 110 so that the far field telemetry communication circuitry 210 instructs the signal propagation tool over the connection 118 or the signal propagation tool may be a separate external component or housed within the external device 102.

In addition to the far field telemetry communication circuitry 210, the external device 102 also includes proximity telemetry communication circuitry 212. The proximity telemetry communication circuitry 212 may be of various forms to interact with the proximity communicator 110. The link between the proximity telemetry communication circuitry 212 and the proximity communicator 110 may be a wired or wireless connection, for example using universal serial bus protocol, Bluetooth® protocol, or other such protocols, that provides data commands to circuitry within the proximity communicator 110 to produce the proximity communication signal. The proximity communicator 110 may then include a near field inductive driver circuit, a signal generator for producing audible tones, a motion signal generator for driving a body thump device, a field producing circuit for driving an electromagnet, and the like that are responsive to the data commands. Alternatively for a wired connection, these circuits may be included in the proximity telemetry communication circuitry 212 to drive the proximity communicator 110 directly.

The external device 102 may include additional communication capabilities that may be provided by far field telemetry communication circuitry 210 or by additional communication circuitry. For instance, the external device 102 may include Wi-Fi connectivity, public switched telephone network connectivity, and so forth to allow for remote communication, particularly where the external device 102 is a patient controlled device.

The external device 102 may include a recharge circuit 214 that generates recharge waveforms to inductively transfer energy to the IMD 104. The recharge circuit 214, for example, may include a coil that is driven by a waveform generator that receives energy from a power supply. The recharge circuit 214 may utilize the coil that may be present within the proximity communicator 110 to deliver the recharge energy.

The memory 204 may be used to store information in use by the processor 202. For instance, the memory 204 may store therapy parameters and/or instructions that are input by a clinician or patient that are to be loaded into the IMD 104. The memory 204 may also store programming that is used by the processor 202 to control the IMD selection procedure of the external device 102 and to control the delivery of the recharge energy. The memory 204 may be of various types, such as volatile, non-volatile, or a combination of the two.

The storage device 206 may be used to store information for a long term and may be of various types such as non-volatile so that the information is retained when the external device 102 is powered off. The storage device 206 may also store programming for the processor 202 that is implemented to control the IMD selection procedure and the delivery of recharge energy. Examples of the storage device 206 include electronic, magnetic, and optical drives including fixed and removable types such as secure digital cards and the like. The storage device 206 and the memory 204 are both examples of computer readable media that may store information in the form of computer programming, data structures, and the like.

The processor 202 performs logical operations to provide a sequence of far field and proximity communications, to control delivery of recharge energy, and to make related decisions such as those of FIGS. 4A-4F, 5A, and 5B to allow far field telemetry communication sessions with the IMD 104 to be established in conjunction with a recharge session. The processor 202 may be of various forms. For instance, the processor 202 may be a general-purpose programmable processor that executes software that is stored on the storage device 206 or elsewhere. Other examples include a dedicated purpose hardware circuit or hard-wired digital logic. The processor 202 may be multiple separate components or processors, dedicated hardware/state machine, and the like. The processor 202 may communicate with the various other components through one or more data buses.

Figure 3:
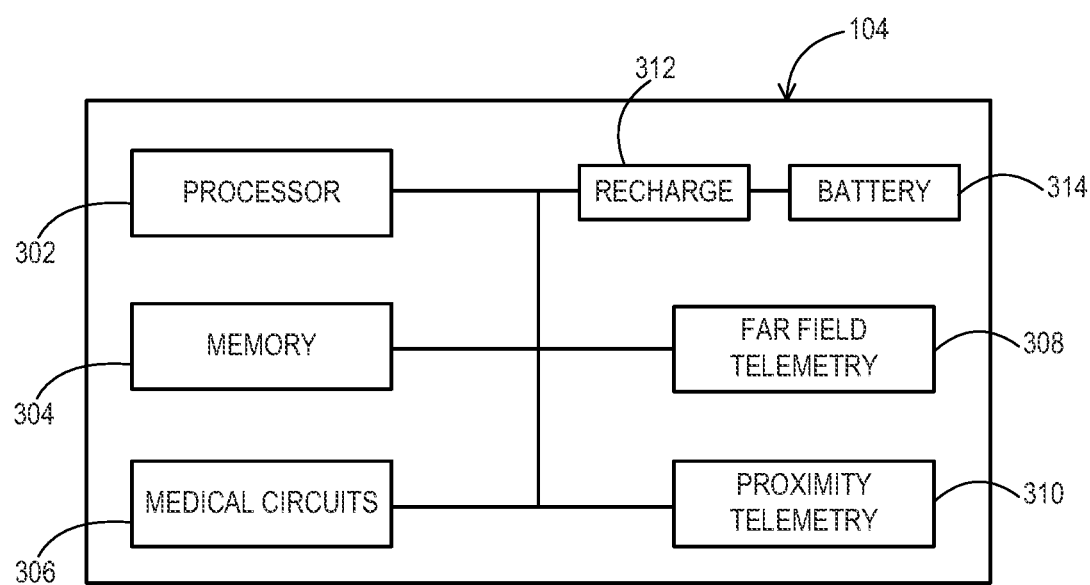
FIG. 3 shows an example of components of an implantable medical device of the medical system.

FIG. 3 shows components of one example of the IMD 104 to be recharged. The IMD 104 includes a processor 302 and a memory 304. The IMD 104 also includes medical circuitry 306 that performs a medical task such as stimulation, drug delivery, monitoring, and the like. The IMD 104 also includes far field telemetry communication circuitry 308 used to establish the far field telemetry communication session with the external device 102 independently of or in conjunction with a recharge session. The far field telemetry communication circuitry 308 may drive a signal propagation tool such as an integral RF antenna.

In addition to the far field telemetry communication circuitry 308, the IMD 104 also includes proximity telemetry communication circuitry 310. The proximity telemetry communication circuitry 310 may be of various forms where for a given system, the type of proximity telemetry communication circuitry 310 matches the type of proximity communicator 110 that the external device 102 includes. Accordingly, the proximity telemetry communication circuitry 310 may be a near field inductive receiver, a microphone for receiving audible tones, an accelerometer or other vibration detection device, a field operable switch such as a magnetic reed switch, and the like.

The IMD 104 also includes a rechargeable battery 314 and a recharge circuit 312 coupled to the battery 314. The recharge circuit 312 may include a coil that inductively couples to the coil of the recharge circuit 214 of the external device 102. The recharge circuit 312 may utilize a dedicated coil or may utilize a coil that is also used by the proximity telemetry communication circuit 310. The recharge circuit 312 may include rectification, filtering, voltage/current limiting, and the like so as to provide an appropriate form of recharge power to the battery 314.

The memory 304 may be used to store information in use by the processor 302 such as programming and data values. The memory 304 may store additional information including therapy parameters that are used to control the medical circuitry 306 as well as recharge parameters that are used to control the recharge circuitry 312. The memory 304 may be of various types such as volatile, non-volatile, or a combination of the two. The memory 304 is also an example of computer readable media that may store information in the form of computer programming, data structures, and the like.

The processor 302 performs logical operations to provide a sequence of far field and proximity communications, to control delivery of recharge energy, and to make related decisions such as those of FIGS. 4-9 to allow far field telemetry communication sessions with the external device 102 to be established independently of and in conjunction with a recharge session. The processor 302 may be of various forms like those discussed above for the processor 202 of the external device 102 and as discussed above may be multiple separate components or processors, dedicated hardware/state machine, and the like. The processor 302 may communicate with the various other components through one or more data buses.

FIGS. 4A-4F, 5A, and 5B describe proximity based communications being used to facilitate far field recharge sessions in conjunction with recharge or status sessions. While these examples show proximity communications being directed from an external device 102 to an IMD 104, it will be appreciated that in some cases the roles may be reversed and the direction of the proximity communications may be reversed whereby the IMD 104 may send proximity communications rather than or in addition to the external device 102 doing so.

Figure 4A:
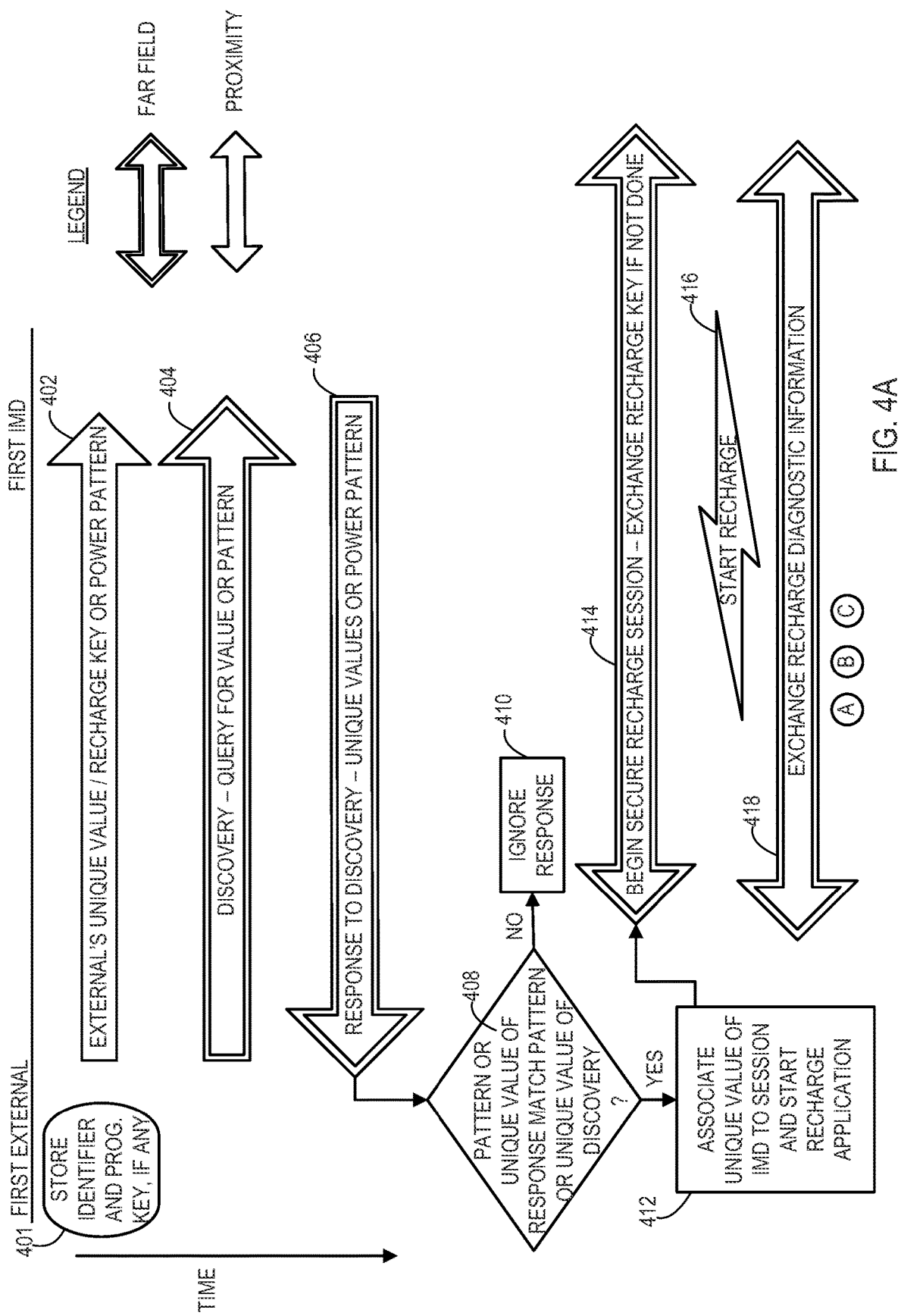
Figure 4A:
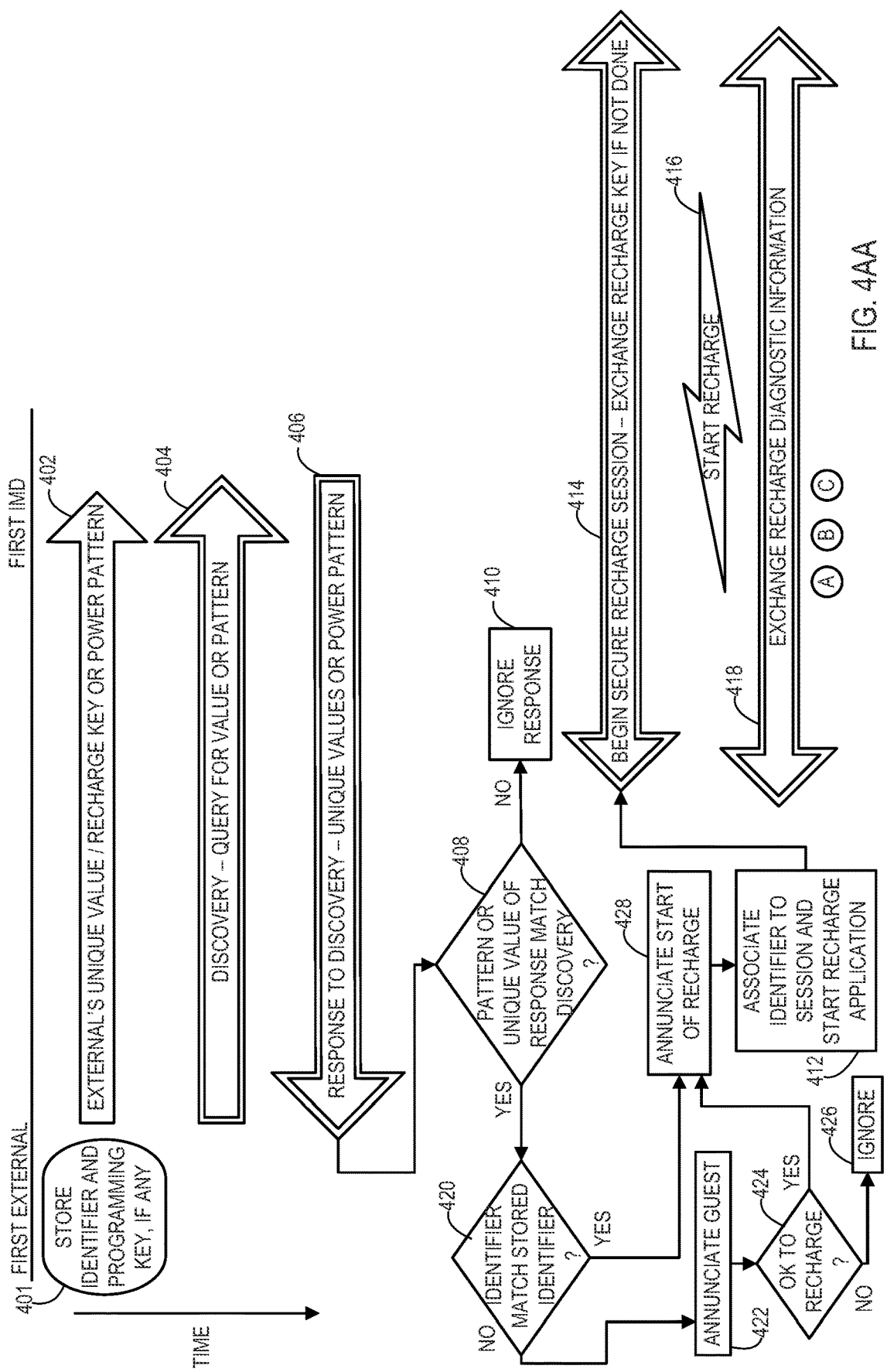

FIG. 4A shows a first example of a procedure to establish a far field telemetry communication session where a unique value and/or key are shared via a proximity communication. The proximity communication may be of a type that can carry data or may be a presence, absence, or pattern of recharge energy. Furthermore, the proximity communication may be bi-directional so that an acknowledgement may be returned as a confirmation of receipt of the data so that a successful initial data transfer via the proximity communication can be completed as a prerequisite to attempting subsequent steps.

Initially, the external device 102 may store an identifier of a program bonded IMD and may also store a programming key for that program bonded IMD as indicated at state 401. For security, some embodiments may preclude far field telemetry communication between external devices 102 and an IMD unless the two are bonded, and utilizing the proximity communication is an example of bonding the two including sharing identifiers and/or programming keys. The identifier and programming key allows the external device 102 to conduct a far field programming session without requiring a proximity communication to occur between the external device and the IMD where the two have already been program bonded and where a programming session is being conducted. The programming key and identifier may have previously been exchanged by virtue of a proximity based process.

In FIG. 4A, a recharge session is desired between the first external device 102 and the first IMD 104 to be recharged. In this particular example, because the user has selected to conduct a recharge session via the external device, the program bond that the external device 102 may have, if any, is not applicable to initiating a far field telemetry communication session in conjunction with a recharge session. In this manner, the far field telemetry communication session in conjunction with a recharge session is initiated by the external device 102 the same for any IMD to be recharged regardless of whether the IMD to be recharged already shares a program bond with the external device 102. The operations of FIG. 4A-4D show that a temporary bond is created between the external device 102 and the IMD 104 to be recharged for purposes of conducting far field telemetry communications during a recharge session with an IMD 104 to be recharged.

The recharge session may be initiated in various ways according to various embodiments. For instance, the external device 102 may present a menu option to a user for beginning a recharge session. As another example, the external device 102 may prompt the user as to whether to begin recharge in response to some event, such as the user plugging in a recharge tool such as the proximity communicator 110 into the external device. As yet another example, the external device 102 may begin the recharge session automatically in response to some event, such as the user plugging in a recharge tool such as the proximity communicator 110 in to the external device.

Initially, the external device 102 may send a proximity communication 402 that includes a value that is unique to the external device 102 to the IMD 104. For example, the unique value may be a device serial number, hardware identification number, randomly generated number, a security key value, a combination, or other such values that may be unique to the external device 102. As another example, the proximity communication 402 may be recharge energy that may be constant, pulsed, or otherwise manipulated so as to be unique. Because this information is transferred through the proximity communication 402, no other nearby IMD will receive this information or pattern of recharge energy. The external device 102 also sends a far field discovery communication 404 shortly before, during, or shortly after sending the proximity communication 402. The IMD 104 as well as other nearby IMDs may receive and respond to this far field discovery communication 404.

In one example, the IMD 104 may respond only to a discovery request that is within a certain time of receiving the proximity communication 402, such as a simultaneous occurrence of the proximity communication 402 and the discovery communication 404 or within a predefined delay from one to the next. In this example, the IMD 104 and potentially other nearby IMDs as well are configured to respond by sending the unique value that each has received via a proximity communication and also by sending a value that is unique to the IMD. For example, this value may be a device serial number, hardware identification number, randomly generated number, a security key value, a combination, or other such values that may be unique to the IMD 104.

Only the far field response communication 406 from the IMD 104 of interest will have the unique value that corresponds to the external device 102. Other IMDs would either have no unique value of an external device to send or would send the unique value of a different external device. Furthermore, in some examples, only those IMDs that receive the discovery communication 404 within a specified time relative to a proximity communication, such as the proximity communication 402 received by the intended IMD 104, bother to respond with a far field response communication such as the far field response communication 406 from the intended IMD 104.

For each far field response communication, the external device 102 attempts to verify the shared unique value by determining whether the unique value being received matches the unique value that was previously sent over the proximity communication 402 at a query operation 408. If a particular response does not include a matching value, then that particular response is ignored at operation 410.

For embodiments using processes such as those of FIG. 4A where discovery via far field telemetry communications is attempted, the external device 102 and IMDs may be configured to apply collision avoidance and backoff algorithms. These algorithms allow devices to re-attempt to send and/or receive expected far field telemetry communications where two devices may attempt to send a far field telemetry communication at the same time such that neither transmission is received and acknowledged. A re-attempt to send the far field telemetry communication occurs by each of the sending devices but at different times on the second attempts because the backoff algorithm of each sending device randomly chooses the time for the re-attempt. This reduces the likelihood of collisions occurring multiple times. Thus, the external device 102 eventually receives a discovery response that has not collided with another. Furthermore, the external device 102 eventually receives a discovery response from the IMD 104 for which proximity communication 402 has been established.

For the response 406 which does have the matching unique value from the proximity communication 402, the external device 102 then associates the value that is unique to the IMD 104 and that is included in the far field response communication 406 to the far field telemetry communication session being established at an association operation 412. The external device 102 may also then execute the appropriate recharge program automatically based on the value that is unique to the IMD 104 where the external device 102 stores associations of such values to recharge applications.

The external device 102 then begins the far field telemetry communication session 414 and the related recharge session 416 with the IMD 104. The external device 102 may communicate during the far field session 414 by using the unique value of the external device 102 of which the IMD 104 is aware to identify the sender of transmissions and/or using the unique value of the IMD 104 to identify the intended recipient of transmissions. Likewise, the IMD may communicate during the far field session 414 by using the unique value of the IMD 104 of which the external device 102 is aware to identify the sender of transmissions and/or using the unique value of the external device 102 to identify the intended recipient of transmissions.

The far field session 414 may be made secure by encrypting the information with an encryption key referred to as the recharge key. This recharge key may have been generated for the session by the external device 102 and included in the proximity communication 402 so that the IMD 104 already has the key. Alternatively, the key may be exchanged in another manner and/or at another time in the sequence such as by using a low power radio frequency communication to minimize the range and thereby provide a level of security for the transfer of the recharge key to the IMD 104. Furthermore, the IMD 104 may provide the recharge key for the secure far field session 414 rather than receiving the key from the external device 102.

During the far field session 414, recharge diagnostic information 418 may be exchanged between the IMD 104 being recharged and the external device 102 that is in control of recharging the IMD 104. This diagnostic information allows the external device 102 to monitor the recharge efficiency, the status of the battery or other status information, and the like. The external device 102 may control the delivery of the recharge energy 416 in response to such diagnostic information such as by increasing or decreasing the level of recharge energy 416, prompting the user to adjust the position the recharge tool, and to eventually terminate the recharge session upon detection of a fully recharged battery 314.

In some embodiments, the exchange of information 418 via far field telemetry communications may occur simultaneously with the delivery of the recharge energy as a result of the far field telemetry communications being significantly out-of-band relative to the recharge energy waveform. However, in other embodiments the exchange of information 418 via far field telemetry communications may instead occur during pauses in delivery of the recharge energy 416.

Figure 4B:
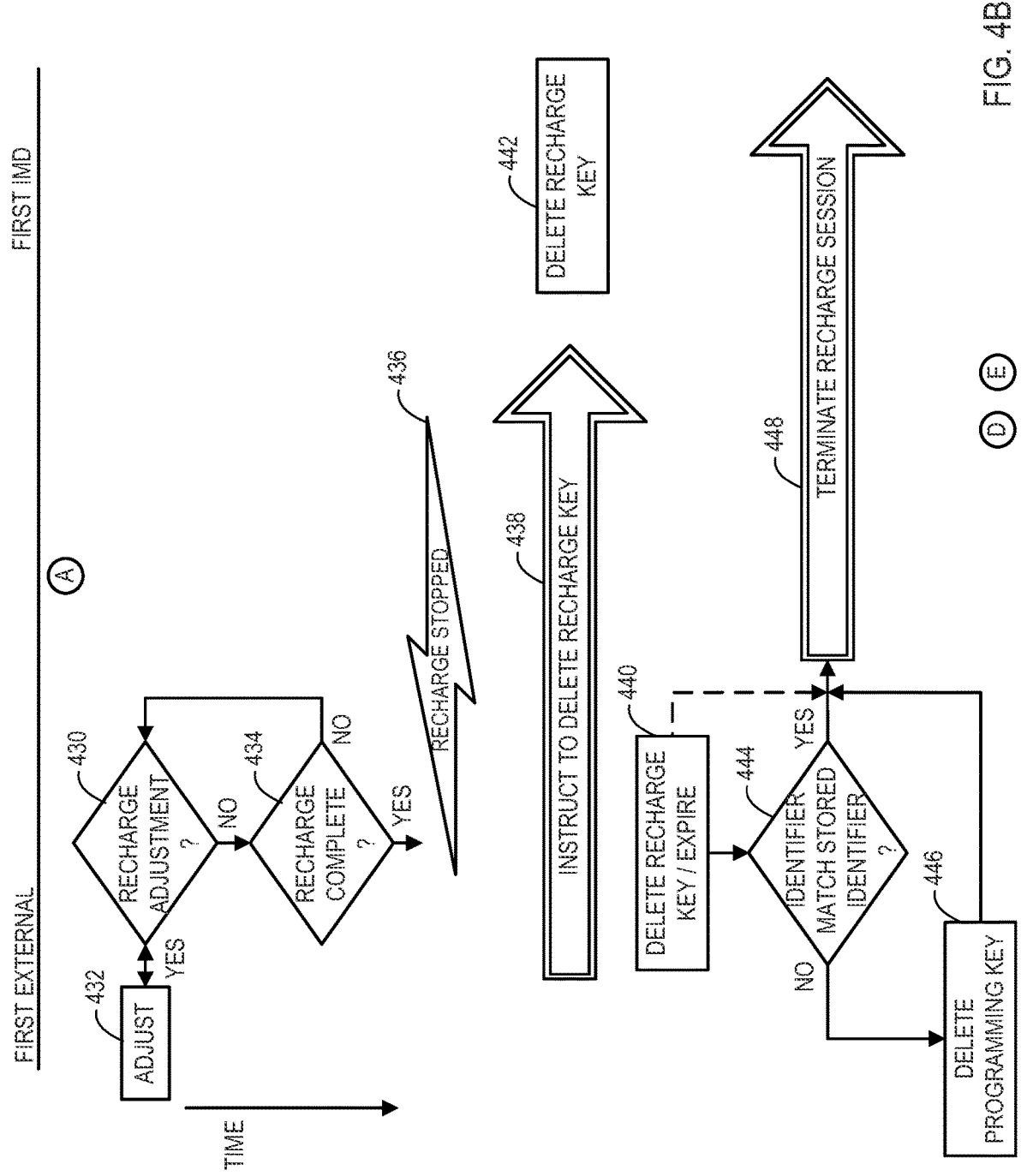
Figure 4C:
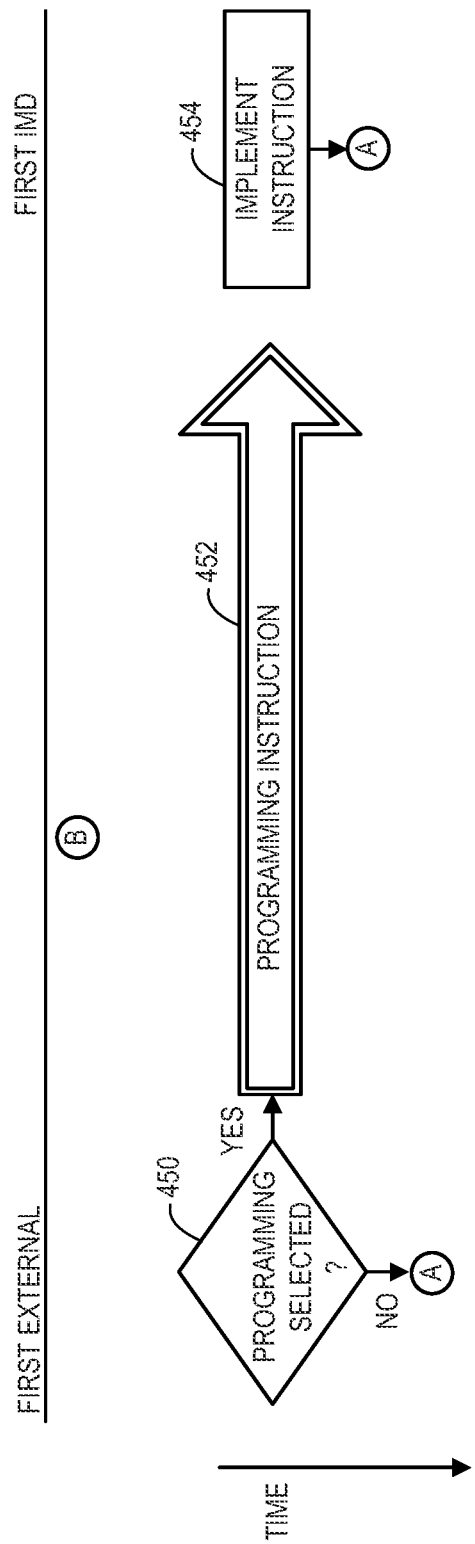
Figure 4D:
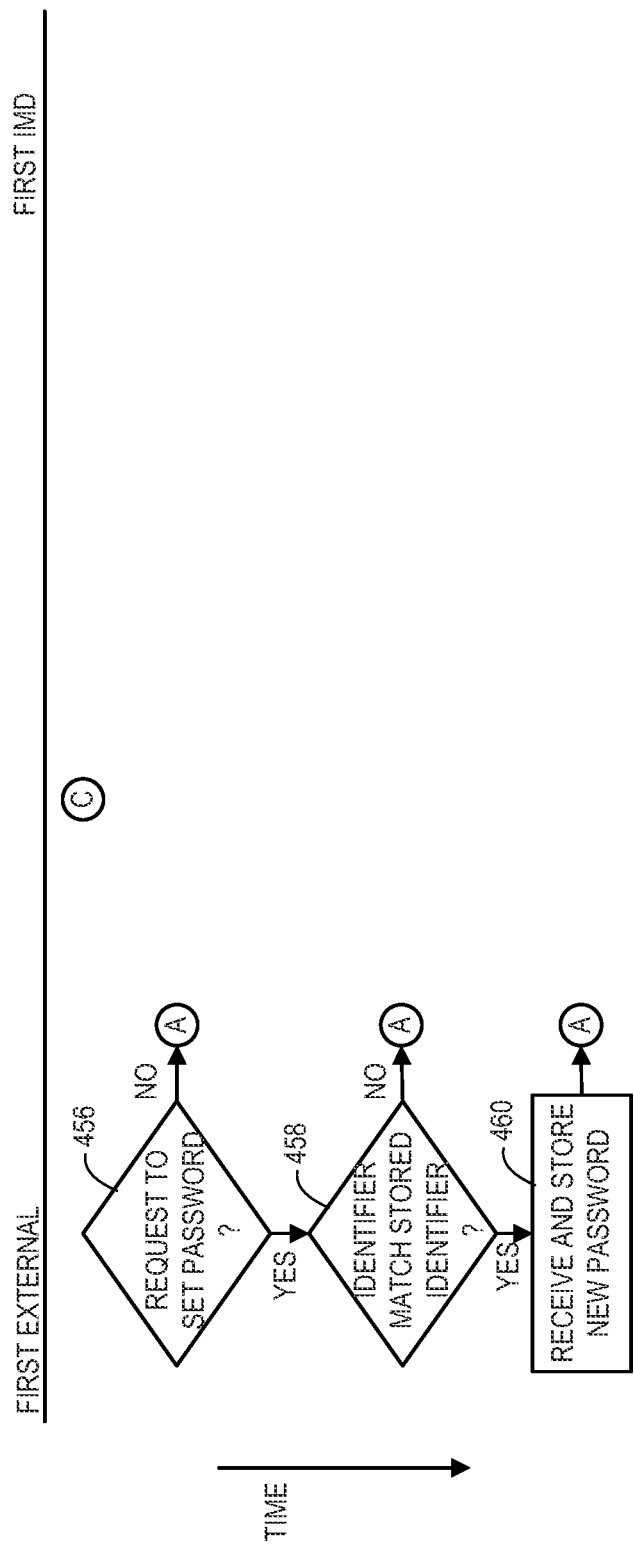

During the exchange of diagnostic information 418 in conjunction with the delivery of recharge energy 416, various additional activities may take place such as those illustrated in FIGS. 4B, 4C, and 4D. These additional activities and figures are discussed in more detail below after the discussion of an alternate manner of initiating the far field and recharge sessions as illustrated in FIG. 4AA.

As with FIG. 4A, in FIG. 4AA the external device 102 may store an identifier of a program bonded IMD and may also store a programming key for that program bonded IMD as indicated at state 401. Furthermore, a recharge session is desired between the first external device 102 and the first IMD 104 to be recharged. Also in this particular example, because the user has selected to conduct a recharge session via the external device, the program bond that the external device 102 may have, if any, is not applicable to initiating a far field telemetry communication session in conjunction with a recharge session. In this manner, the far field telemetry communication session in conjunction with a recharge session is initiated by the external device 102 of this example in the same way for any IMD to be recharged regardless of whether the IMD to be recharged already shares a program bond with the external device 102. The operations of FIG. 4AA-4D show that a temporary bond is created between the external device 102 and the IMD 104 to be recharged for purposes of conducting far field telemetry communications during a recharge session with an IMD 104 to be recharged.

Initially in FIG. 4AA, the external device 102 may send a proximity communication 402 such as that from FIG. 4A that includes a value that is unique to the external device 102 to the IMD 104. Because this information is transferred through the proximity communication 402, no other nearby IMD will receive this information or pattern of recharge energy. The external device 102 also sends a far field discovery communication 404 shortly before, during, or shortly after sending the proximity communication 402. The IMD 104 as well as other nearby IMDs may receive and respond to this far field discovery communication 404.

In one example, the IMD 104 may respond only to a discovery request that is within a certain time of receiving the proximity communication 402, such as a simultaneous occurrence of the proximity communication 402 and the discovery communication 404 or within a predefined delay from one to the next. In this example, the IMD 104 and potentially other nearby IMDs as well are configured to respond by sending the unique value that each has received via a proximity communication and also by sending a value that is unique to the IMD as discussed above in relation to FIG. 4A.

Only the far field response communication 406 from the IMD 104 of interest will have the unique value that corresponds to the external device 102. Other IMDs would either have no unique value of an external device to send or would send the unique value of a different external device. Furthermore, in some examples, only those IMDs that receive the discovery communication 404 within a specified time relative to a proximity communication, such as the proximity communication 402 received by the intended IMD 104, bother to respond with a far field response communication such as the far field response communication 406 from the intended IMD 104.

For each far field response communication, the external device 102 attempts to verify the shared unique value by determining whether the unique value being received matches the unique value that was previously sent over the proximity communication 402 at a query operation 408. If a particular response does not include a matching value, then that particular response is ignored at operation 410. As in FIG. 4A, the external device 102 and IMDs of FIG. 4AA may also be configured to apply collision avoidance and backoff algorithms.

For the response 406 which does have the matching unique value from the proximity communication 402, the external device 102 then detects at a query operation 420 whether the identifier of the IMD 104 that is provided in the response matches the identifier that is stored per state 401. The stored identifier reflects which IMD has a program bond with the external device 102. It may be desirable to provide some level of notification to the user that the IMD 104 to be recharged is considered a guest IMD as opposed to being the program bonded IMD. For instance, the user may have obtained the wrong external device 102 such as in a setting where multiple external devices are present. Thus, where the identifier that has been received via discovery does not match the stored identifier, then the external device 102 annunciates that the IMD is a guest at an annunciation operation 422. This may be a visual display, an audible message, or a combination so that the user is made aware.

The external device 102 may then detect whether the user selects that it is appropriate to continue with the far field and recharging session with the current external device 102 and IMD 104. If it is not acceptable to continue, then the recharge process terminates by the external device 102 terminating further interaction with the IMD 104 at an ignore operation 426. If it is acceptable to continue, then the external device 102 may annunciate that the recharge process is beginning at an annunciation operation 428. In other embodiments, the far field and recharging sessions may continue after the annunciation that the IMD 104 is a guest without first querying the user for permission. Where the identifier received via the discovery response does match the identifier that is stored, indicating that the IMD 104 to be recharged is the program bonded IMD, then the external device 102 may annunciate that the recharge process is beginning at the annunciation operation 428.

The external device 102 then associates the value that is unique to the IMD 104 and that is included in the far field response communication 406 to the far field telemetry communication session being established at an association operation 412. The external device 102 may also then execute the appropriate recharge program automatically based on the value that is unique to the IMD 104 where the external device 102 stores associations of such values to recharge applications.

The external device 102 then begins the far field telemetry communication session 414 and the related recharge session 416 with the IMD 104. The far field session 414 may be made secure by encrypting the information with the recharge key. As with FIG. 4A, this recharge key may have been generated for the session by the external device 102 and included in the proximity communication 402 so that the IMD 104 already has the key. Alternatively, the recharge key may be exchanged in another manner and/or at another time in the sequence such as by using a low power radio frequency communication to minimize the range and thereby provide a level of security for the transfer of the recharge key to the IMD 104. Furthermore, the IMD 104 may provide the recharge key for the secure far field session 414 rather than receiving the key from the external device 102.

During the far field session 414, recharge diagnostic information 418 may be exchanged between the IMD 104 being recharged and the external device 102 that is in control of recharging the IMD 104. The exchange of information 418 via far field telemetry communications may occur simultaneously with the delivery of the recharge energy or may instead occur during pauses in delivery of the recharge energy 416.

From FIG. 4A or FIG. 4AA, the operations may proceed to those shown at FIGS. 4B, 4C, and/or 4D. FIG. 4B shows that during the recharge session, the external device 102 may detect at a query operation 430 whether recharge adjustments are necessary based on the diagnostic information being received from the IMD 104. If an adjustment is needed, the external device 102 makes a change at an adjustment operation 432. This may involve changing the recharge energy, prompting the user to move the recharge tool, and the like. The external device 102 also detects at a query operation 434 whether the recharge process has completed based on the battery reaching a full charge. If recharging has completed, the external device 102 then stops the recharge energy 436.

Because the far field telemetry communication session is based on a temporary bond during the recharge session, the external device 102 may submit an instruction 438 via far field telemetry communication that the IMD 104 should delete the recharge key. The IMD 104 responds by deleting the recharge key at a deletion operation 442. Similarly, the external device 102 deletes the recharge key at a deletion operation 440. Rather than an explicit instruction and act of deleting the recharge key at both the external device 102 and/or the IMD 104, the recharge key may be assigned an expiration time that coincides with an expected time that recharge may be completed so that the recharge key becomes non-operational once expired after the recharge session ends. By deleting the recharge key or allowing it to expire, current and future use of the temporary bond via the recharge key is discontinued, and the external device 102 will subsequently enter into a new temporary bond for recharging with the same or different IMD.

According to some embodiments, at the time of deleting the recharge key, the external device 102 also performs a termination 448 of the far field telemetry communication session with the IMD 104 with no further action being taken. However, according to other embodiments, the external device 102 may take additional steps to safeguard against inadvertent programming. As the external device 102 retains the program bond during a recharge session where a temporary bond with a guest IMD 104 has occurred, upon the conclusion of the recharge session the patient corresponding to the guest IMD 104 may still have physical possession of the external device 102. As discussed in relation to FIG. 4C, during a recharge session, the far field telemetry communication session may also allow programming to be done such as to allow the patient to adjust therapy. So, a patient may not realize that the recharge session has terminated and may attempt to make a therapy adjustment to their IMD 104. However, because the recharge session has terminated, the external device 102 no longer has a far field telemetry communication session with the IMD 104 of the patient currently using the external device 102. To prevent, the external device 102 from establishing a programming session with the IMD that has the program bond, which is not the IMD of the patient still using the external device 102, the external device 102 may eliminate the program bond by the end of the recharge session.

As shown in FIG. 4B, the external device 102 detects at a query operation 444 whether the identifier that has been received via discovery matches the stored identifier. Here, the external device 102 is determining whether the IMD 104 that has been temporarily bonded during the recharge session is also the IMD that is program bonded to the external device 102. If the identifier does match, then the IMD 104 of the recharge session is the IMD that is program bonded so the external device 102 proceeds to terminate the recharge session and related far field session with no further action being taken. However, if the identifier does not match, then the IMD 104 of the recharge session is not the IMD that is program bonded so the external device 102 proceeds to delete the programming key at the external device 102 at a deletion operation 446. While this process of deleting the programming key is shown to occur at the end of the recharge session, it will be appreciated that the programming key may be deleted at any time during the recharge session.

The recharge session and related far field session may then be terminated with the IMD 104. In this embodiment, the programming key of the IMD 104 is not deleted if an identifier match occurs in query operation 444 and the IMD 104 thereby maintains a program bond with an external device other than the external device 102 so that the IMD 104 will not be required to re-establish a program bond at the next session with the external device to which the IMD 104 is program bonded.

FIG. 4C shows that during the recharge session the user of the external device 102 may select that programming be done. The external device 102 detects at a query operation 450 that the user has selected an option to adjust the programming. The external device 102 then uses the far field telemetry communication session that is being used to exchange recharge diagnostics to instead exchange programming instructions 452. The IMD 104 being recharged receives and acts on the instruction at an implementation operation 554.

FIG. 4D shows that during the recharge session, the user of the external device 102 that has confirmed that the recharge session is with an IMD 104 that is program bonded to the external device 102 may select to perform operations that would otherwise require additional forms of security. For instance, as shown in FIG. 4D, the user of the external device 102 may change a password for the external device 102 where that password may be required to create a programming session with the program bonded IMD 104 or to change the password of the external device 102 outside of a recharge session. The password is not required to create a recharge session because the physical proximity communication ensures that the correct IMD is included in the far field telemetry communications. The correct IMD being confirmed and which is program bonded to the external device 102 satisfies security concerns because it is presumed that the patient who should have access to programming and security features of the external device 102 is the same patient who also possesses the program bonded IMD currently in the recharge session with the external device 102.

The external device 102 detects at a query operation 456 that the user has selected an option that requests a change to the password of the external device 102. The external device 102 then detects at a query operation 458 whether the identifier of the IMD 104 being recharged which was received via the discovery response matches the identifier that is stored for the program bond. If the identifier does not match, then the external device 102 ignores the request to change the password. However, if the identifier does match, then the external device 102 has satisfactorily determined that that user of the external device 102 is the rightful user who should have access to secure features. Therefore, the external device 102 receives a new password from the user and stores it in memory to replace the forgotten password at a password operation 460.

FIG. 4E shows a point in time after the IMD 104 has been recharged as a guest to an external device 102 where the IMD 104 becomes a party to a programming session with a second external device to which the IMD 104 is program bonded. Because the IMD 104 was not required to delete the programming session key that is shared with the second external device to which the IMD 104 is program bonded, a far field programming session is possible without repeating device discovery and programming key assignment. This presumes that the second external device has not recharged a guest IMD which may have caused the second external device to delete the programming key in accordance with FIG. 4B.

Initially, the second external device begins a far field telemetry communication programming session with the IMD 104 by sending a wake-up signal. In some embodiments the wake-up signal may be a repeated far field telemetry communication so that the IMD 104 eventually listens for and receives the signal. In other embodiments, the second external device may utilize a proximity wake-up signal via a proximity communicator in physical proximity to the IMD 104. The IMD 104 responds to the second external device with an acknowledgement 465, and the second external device and the IMD 104 then begin exchanging information 466 securely using the programming key that continues to be stored by both devices. The second external device then closes the secure far field session 468 with the IMD 104.

Figure 4F:
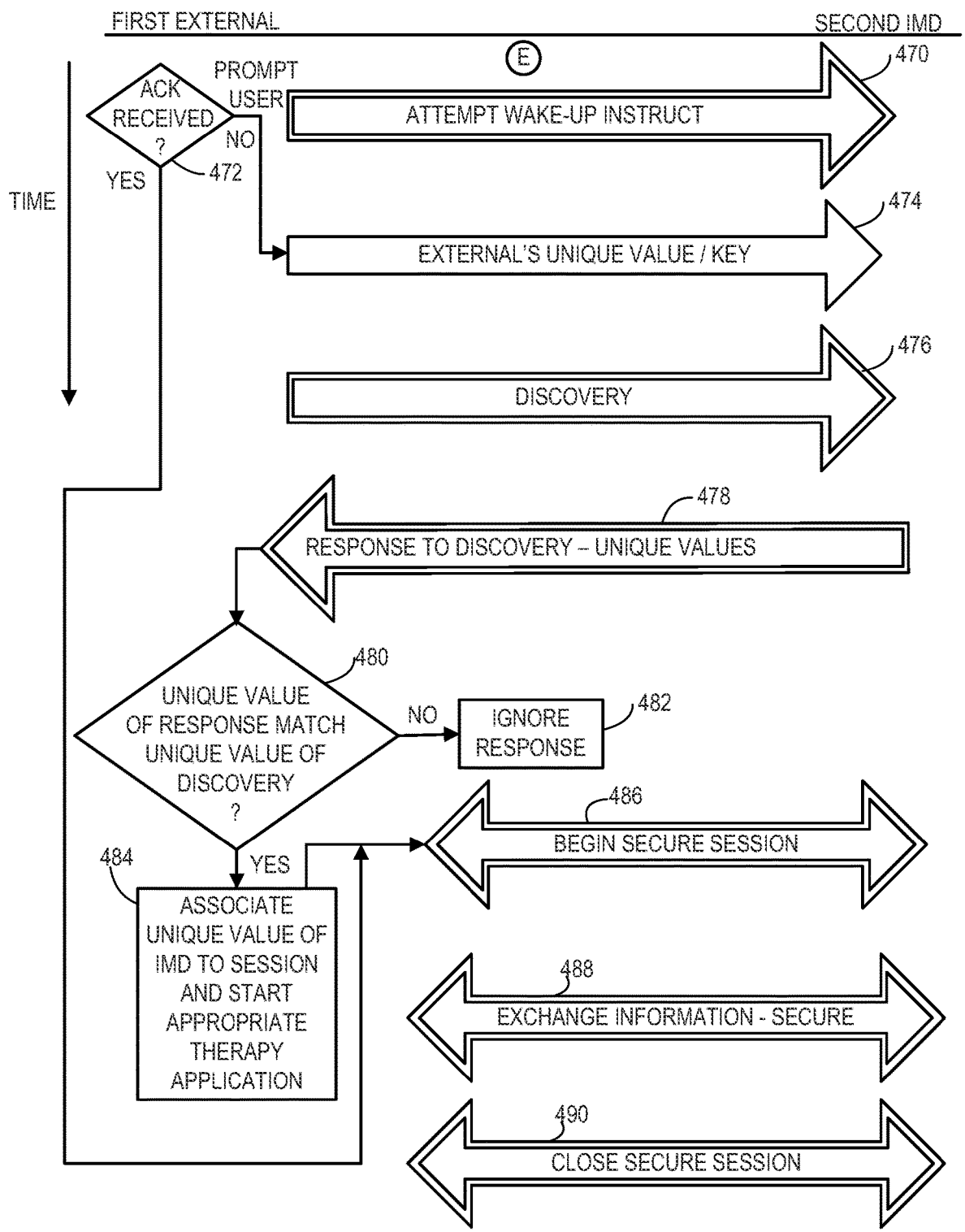

FIG. 4F shows a point in time after the IMD 104 has been recharged as a guest to an external device 102 where the external device 102 becomes a party to a programming session with a second IMD to which the external device 102 has been previously program bonded. In this embodiment the external device 102 deleted the programming session key that is shared with the second IMD to which the external device 102 was program bonded as shown in FIG. 4B. A far field programming session between the previously bonded external device 102 and second IMD repeats device discovery and programming key assignment even though the second IMD may have retained the programming key from the initial program bond with the external device 102.

Initially, the external device 102 may attempt to wake-up and instruct the second IMD to respond. However, because the current key in use by the external device 102 has replaced the previous programming key which the second IMD continues to retain, the second IMD cannot decrypt secure communications from the external device 102. The external device at a query operation 472 then detects whether an acknowledgement has been received. For instances where the external device 102 has not recharged a guest IMD 104, then the programming key of the external device 102 matches that of the second IMD and the IMD provides the acknowledgement. In that case, the external device 102 begins the secure far field programming session 486 with the IMD. However, where the external device 102 has deleted the programming key and replaced it with a different programming key that the second IMD has yet to acquire, the external device 102 does not receive an acknowledgement and initiates a device discovery process.

Initially, the external device 102 may send a proximity communication 474 that includes a value that is unique to the external device 102 to the second IMD. To do so, the external device 102 may first prompt the user to place the proximity communicator 110 in proximity of the second IMD. Because this information is transferred through the proximity communication 474, no other nearby IMD will receive this information or pattern of recharge energy. The external device 102 also sends a far field discovery communication 476 shortly before, during, or shortly after sending the proximity communication 402. The second IMD as well as other nearby IMDs may receive and respond to this far field discovery communication 476.

In one example, the second IMD may respond only to a discovery request that is within a certain time of receiving the proximity communication 474, such as a simultaneous occurrence of the proximity communication 474 and the discovery communication 476 or within a predefined delay from one to the next. In this example, the second IMD and potentially other nearby IMDs as well are configured to respond by sending the unique value that each has received via a proximity communication and also by sending a value that is unique to the IMD. For example, this value may be a device serial number, hardware identification number, randomly generated number, a security key value, a combination, or other such values that may be unique to the second IMD.

Only the far field response communication 478 from the IMD 104 of interest will have the unique value that corresponds to the external device 102. Other IMDs would either have no unique value of an external device to send or would send the unique value of a different external device. Furthermore, in some examples, only those IMDs that receive the discovery communication 476 within a specified time relative to a proximity communication, such as the proximity communication 474 received by the intended second IMD, bother to respond with a far field response communication such as the far field response communication 478 from the intended second IMD.

For each far field response communication, the external device 102 attempts to verify the shared unique value by determining whether the unique value being received matches the unique value that was previously sent over the proximity communication 474 at a query operation 480. If a particular response does not include a matching value, then that particular response is ignored at operation 482.

Here, the external device 102 and IMDs may be configured to apply collision avoidance and backoff algorithms. Thus, the external device 102 eventually receives a discovery response that has not collided with another. Furthermore, the external device 102 eventually receives a discovery response from the second IMD for which proximity communication 474 has been established.

For the response 478 which does have the matching unique value from the proximity communication 474, the external device 102 then associates the value that is unique to the second IMD and that is included in the far field response communication 478 to the far field telemetry communication session being established at an association operation 484. The external device 102 may also then execute the appropriate therapy program automatically based on the value that is unique to the second IMD where the external device 102 stores associations of such values to therapy applications.

The external device 102 then begins the far field telemetry communication session 486 and with the second IMD. The external device 102 may communicate during the far field session 486 by using the unique value of the external device 102 of which the second IMD is aware to identify the sender of transmissions and/or using the unique value of the second IMD to identify the intended recipient of transmissions. Likewise, the second IMD may communicate during the far field session 486 by using the unique value of the second IMD of which the external device 102 is aware to identify the sender of transmissions and/or using the unique value of the external device 102 to identify the intended recipient of transmissions.

The far field session 486 may be made secure by encrypting the information with the newly exchanged programming key which has replaced the programming key that has been retained by the second IMD. This new programming key creates a new program bond between the external device 102 and the second IMD. This new programming key may have been generated for the session by the external device 102 and included in the proximity communication 474 so that the IMD 104 already has the new programming key. Alternatively, the new programming key may be exchanged in another manner and/or at another time in the sequence such as by using a low power radio frequency communication to minimize the range and thereby provide a level of security for the transfer of the new programming key to the second IMD.

Using the programming key, the external device 102 and the second IMD exchange information 488 such as programming information over the secure far field telemetry communications. Once complete, the external device 102 and the second IMD close the secure far field session 490 while both devices retain the new programming key to preserve the program bond for future programming sessions.

Figure 5A:
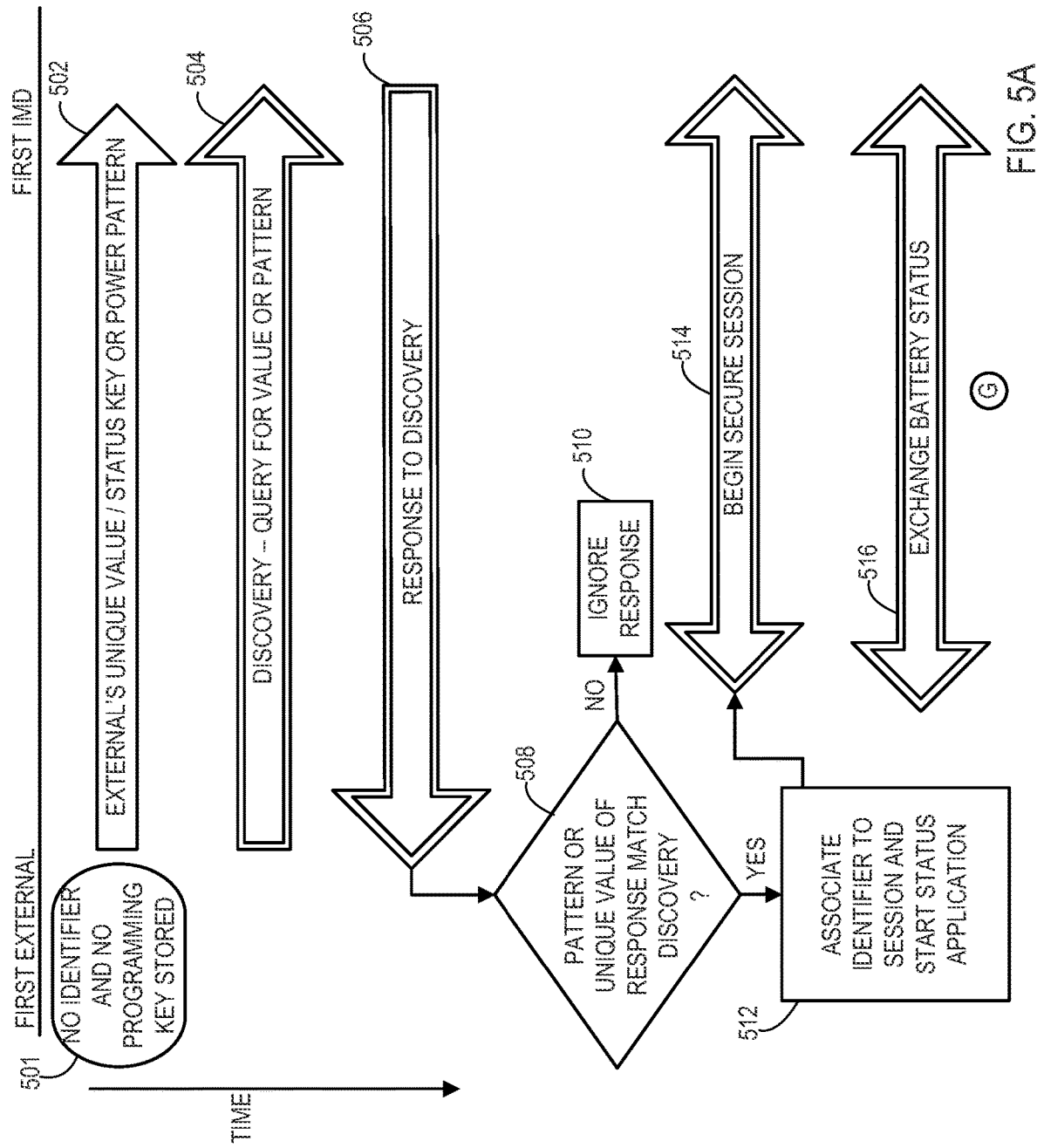
FIGS. 5A and 5B show another example of operations of the external device implantable medical device of the medical system.
Figure 5B:
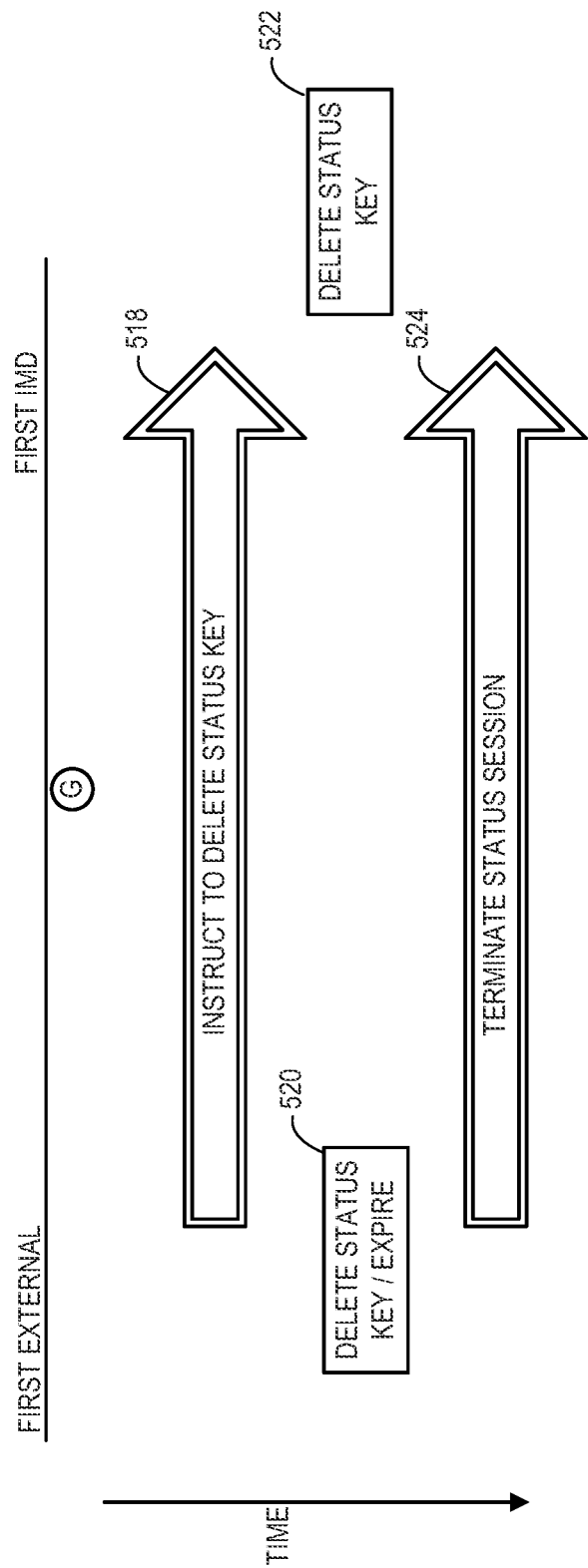

FIGS. 5A and 5B show an example of logical operations for an external device 102 to be used to check the status of a guest implant by creating a temporary bond. In this example, the external device 102 lacks a program bond with any IMD as indicated by state 501 where no programming key or identifier is stored in advance of the status session.

Initially, the external device 102 may send a proximity communication 502 that includes a value that is unique to the external device 102 to the IMD 104. For example, the unique value may be a device serial number, hardware identification number, randomly generated number, a security key value, a combination, or other such values that may be unique to the external device 102. Because this information is transferred through the proximity communication 502, no other nearby IMD will receive this information or pattern of recharge energy. The external device 102 also sends a far field discovery communication 504 shortly before, during, or shortly after sending the proximity communication 502. The IMD 104 as well as other nearby IMDs may receive and respond to this far field discovery communication 504.

In one example, the IMD 104 may respond only to a discovery request that is within a certain time of receiving the proximity communication 502, such as a simultaneous occurrence of the proximity communication 502 and the discovery communication 504 or within a predefined delay from one to the next. In this example, the IMD 104 and potentially other nearby IMDs as well are configured to respond by sending the unique value that each has received via a proximity communication and also by sending a value that is unique to the IMD. For example, this value may be a device serial number, hardware identification number, randomly generated number, a security key value, a combination, or other such values that may be unique to the IMD 104.

Only the far field response communication 506 from the IMD 104 of interest will have the unique value that corresponds to the external device 102. Other IMDs would either have no unique value of an external device to send or would send the unique value of a different external device. Furthermore, in some examples, only those IMDs that receive the discovery communication 504 within a specified time relative to a proximity communication, such as the proximity communication 502 received by the intended IMD 104, bother to respond with a far field response communication such as the far field response communication 506 from the intended IMD 104.

For each far field response communication, the external device 102 attempts to verify the shared unique value by determining whether the unique value being received matches the unique value that was previously sent over the proximity communication 502 at a query operation 508. If a particular response does not include a matching value, then that particular response is ignored at operation 510.

Here, the external device 102 and IMDs may be configured to apply collision avoidance and backoff algorithms. Thus, the external device 102 eventually receives a discovery response that has not collided with another. Furthermore, the external device 102 eventually receives a discovery response from the IMD 104 for which proximity communication 502 has been established.

For the response 506 which does have the matching unique value from the proximity communication 502, the external device 102 then associates the value that is unique to the IMD 104 and that is included in the far field response communication 506 to the far field telemetry communication session being established at an association operation 512. The external device 102 may also then execute the appropriate recharge program automatically based on the value that is unique to the IMD 104 where the external device 102 stores associations of such values to recharge applications.

The external device 102 then begins the far field telemetry communication status session 514 with the IMD 104. The external device 102 may communicate during the far field status session 514 by using the unique value of the external device 102 of which the IMD 104 is aware to identify the sender of transmissions and/or using the unique value of the IMD 104 to identify the intended recipient of transmissions. Likewise, the IMD may communicate during the far field session 514 by using the unique value of the IMD 104 of which the external device 102 is aware to identify the sender of transmissions and/or using the unique value of the external device 102 to identify the intended recipient of transmissions.

The far field status session 514 may be made secure by encrypting the information with an encryption key referred to as the status key. This status key may have been generated for the session by the external device 102 and included in the proximity communication 502 so that the IMD 104 already has the key. Alternatively, the key may be exchanged in another manner and/or at another time in the sequence such as by using a low power radio frequency communication to minimize the range and thereby provide a level of security for the transfer of the recharge key to the IMD 104. Furthermore, the IMD 104 may provide the status key for the secure far field status session 514 rather than receiving the key from the external device 102.

During the secure far field status session, status information 516 such as status of the battery as well as other items of status information may be exchanged between the external device 102 and the IMD 104. This may provide information to the external device 102 regarding the battery without entering a recharge session. From the status information, the user may decide to subsequently initiate a recharge session as described above in relation to FIG. 4A or FIG. 4AA.

Once the status information 516 has been exchanged, the external device 102 may then provide an instruction 518 to delete the status session key as shown in FIG. 5B. The IMD 104 responds by deleting the status key at a deletion operation 522 while the external device deletes the status key at a deletion operation 520 to maintain the temporary nature of the bond for the status session. Alternatively, the status key may be assigned an expiration time so that the status key expires without the external device 102 explicitly deleting the status key, where the status key expiration is set to a time where the status session is expected to have terminated. The external device 102 then terminates the status session 524. The IMD 104 retains the program bond key so that a programming session may be subsequently established with an external device that has a program bond with the IMD 104 without repeating the discovery and programming key assignment process.

While embodiments have been particularly shown and described, it will be understood by those skilled in the art that various other changes in the form and details may be made therein without departing from the spirit and scope of the invention.

What is claimed is:

1. An external device, comprising:
  a memory storing an identifier corresponding to a program bonded implantable medical device and a programming session key;
  a recharge circuit;
  a far field telemetry circuit; and
  a processor configured to:
    send a recharge session key to a first implantable device that is not program bonded by the identifier stored in the memory,
    receive a second identifier and determine if the second identifier matches the identifier stored in the memory,
    send recharge energy during a recharge session to the first implantable medical device using the recharge circuit if the second identifier does not match the identifier stored in the memory and is from the first implantable medical device,
    exchange information related to the recharge session with the first implantable device using the recharge session key via the far field telemetry circuit while the programming session key remains stored in the memory,
    detect user input to compare the second identifier and the identifier stored in the memory to satisfy security concerns;
    ignore the request if the second identifier is different than the identifier stored in the memory,
    provide the user access to secure features if the second identifier is stored in the memory; and
    exchange, at a time after the recharge session, programming information with a second implantable device using the programming session key via the far field telemetry circuit.

2. The external device of claim 1, wherein the processor discontinues current and future use of the recharge session key upon termination of the recharge session.

3. The external device of claim 2, wherein the processor discontinues future use of a prior programming session key stored in the memory upon termination of the recharge session.

4. The external device of claim 3, wherein the processor places the programming session key in the memory after termination of the recharge session.

5. The external of claim 1, wherein the processor exchanges the second identifier via the far field telemetry circuit.

6. The external device of claim 1, further comprising a proximity connection circuit and wherein the processor sends the recharge session key using the proximity connection circuit.

7. The external device of claim 1, wherein the processor sends programming information during the recharge session by using the recharge session key via the far field telemetry circuit.

8. The external device of claim 1, wherein the far field telemetry circuit comprises an RF antenna.

9. A method of operation of an external device, comprising:
- storing both an identifier corresponding to a program bonded implantable medical device and a programming session key in a memory at the external device;
- sending a recharge session key by the external device to a first implantable medical device that is not program bonded to the external device;
- receiving a second identifier and determining if the second identifier that is received matches the identifier stored in the memory;
- transmitting recharge energy from the external device to the first implantable medical device during a recharge session using a recharge circuit if the second identifier that is received does not match the identifier stored in the memory and is from the first implantable medical device;
- exchanging information related to the recharge session of the first implantable medical device with the first implantable medical device using the recharge session key via a far field telemetry circuit while the programming session key remains stored in the memory of the external device;
- detecting user input to compare the second identifier and the identifier stored in the memory to satisfy security concerns;
- ignoring the request if the second identifier is different than the identifier stored in the memory;
- providing the user access to secure features if the second identifier is stored in the memory; and
- exchanging, at a time after the recharge session, programming information with a second implantable medical device using the programming session key via the far field telemetry circuit.

10. The method of claim 9, further comprising discontinuing current and future use of the recharge session key upon termination of the recharge session.

11. The method of claim 10, further comprising discontinuing future use by the external device of a prior programming session key previously used by the external device upon termination of the recharge session.

12. The method of claim 11, further comprising sharing the programming session key with the second implantable medical device after termination of the recharge session.

13. The method of claim 9, wherein receiving the second identifier occurs via the far field telemetry circuit.

14. The method of claim 9, further comprising sending the recharge session key using a proximity connection circuit.

15. The method of claim 9, wherein exchanging programming information during the recharge session occurs by using the recharge session key via the far field telemetry circuit.

16. The method of claim 9, wherein the far field telemetry circuit comprises an RF antenna.

17. A system comprising:
- a first implantable medical device;
- a second implantable medical device; and
- an external device that comprises:
  - a memory storing an identifier corresponding to a program bonded implantable medical device and a programming session key;
  - a recharge circuit;
  - a far field telemetry circuit; and
  - a processor configured to:
  send a recharge session key to the first implantable medical device,
  - receive a second identifier and determine if the second identifier that is received matches the identifier stored in memory,
  - transmit recharge energy to the first implantable medical device during a recharge session using the recharge circuit if the second identifier does not match the identifier stored in the memory and is from the first implantable medical device,
  - exchange information related to the recharge session for the first implantable medical device with the first implantable medical device using the recharge session key via the far field telemetry circuit while the programming session key remains stored in the memory,
  - user input compare the second identifier and the identifier stored in memory to satisfy security concerns,
  - ignore the request if the second identifier is different than the identifier stored in the memory,
  - provide the user access to secure features if the second identifier is stored in the memory, and
  - exchange, at times other than during the recharge session, programming information with the second implantable medical device using the programming session key via the far field telemetry circuit.

18. The system of claim 17, wherein the processor discontinues current and future use of the recharge session key upon termination of the recharge session.

19. The system of claim 18, wherein the processor discontinues future use of a prior programming session key stored in the memory upon termination of the recharge session.

20. The system of claim 19, wherein the processor places the programming session key in the memory after termination of the recharge session.

* * * * *